(12) United States Patent
Rheinberger et al.

(10) Patent No.: US 6,353,039 B1
(45) Date of Patent: Mar. 5, 2002

US006353039B1

(54) POLYMERIZABLE COMPOSITE MATERIAL

(75) Inventors: Volker Rheinberger, Vaduz (LI); Ulrich Salz, Lindau (DE); Wolfram Höland, Schaan (LI); André Rumphorst, Vaduz (LI); Kurt Grabher, Feldkirch (AT); Urs Karl Fischer, Arbon; Marcel Schweiger, Chur, both of (CH); Norbert Moszner, Eschen (LI)

(73) Assignee: Ivoclar AG (LI)

( * ) Notice: Subject to any disclaimer, the term of this patent is extended or adjusted under 35 U.S.C. 154(b) by 0 days.

(21) Appl. No.: 09/209,905

(22) Filed: Dec. 11, 1998

Related U.S. Application Data

(60) Provisional application No. 60/094,018, filed on Jul. 24, 1998.

(30) Foreign Application Priority Data

Dec. 15, 1997 (DE) .......................... 197 57 645

(51) Int. Cl.$^7$ .......................... A61K 6/083; C08K 3/22
(52) U.S. Cl. .................. 523/109; 523/116; 523/115; 524/404; 524/433; 524/443; 524/494; 524/779
(58) Field of Search .................. 523/109, 116, 523/115; 524/405, 433, 443, 494, 779; 100/35; 501/32, 63, 64, 69, 70

(56) References Cited

U.S. PATENT DOCUMENTS

| 4,861,808 A | | 8/1989 | Billington et al. .......... 523/116 |
| 5,176,747 A | * | 1/1993 | Panzera et l. ................. 106/35 |
| 5,354,785 A | * | 10/1994 | Rheinberger et al. ....... 523/116 |
| 5,426,134 A | * | 6/1995 | Rheunberger et al. ...... 523/118 |
| 5,432,130 A | * | 7/1995 | Rheinberger et al. ......... 501/32 |
| 5,539,017 A | * | 7/1996 | Rheinberger et al. ....... 523/116 |
| 5,618,763 A | * | 4/1997 | Frank et al. .................... 501/5 |
| 5,698,019 A | * | 12/1997 | Frank et al. .................. 106/35 |
| 5,698,482 A | * | 12/1997 | Frank et al. .................. 510/10 |
| 6,180,688 B1 | * | 1/2001 | Rheinberger et al. ....... 523/116 |

FOREIGN PATENT DOCUMENTS

EP                2468435 AZ  *  1/1992

* cited by examiner

*Primary Examiner*—Margaret Medley
(74) *Attorney, Agent, or Firm*—Nixon Peabody LLP

(57) ABSTRACT

A composite material is described which contains polymerizable monomers plus a special transparent glass having high release of calcium ions and fluorine ions and, because of this release property and in particular of its optical properties, can be used as a restoration material in dentistry.

7 Claims, No Drawings

POLYMERIZABLE COMPOSITE MATERIAL

This application claims priority benefit of U.S. patent application Ser. No. 60/094,018, filed on Jul. 24, 1998, which is hereby incorporated by reference.

The invention relates to polymerizable composite material which contains a special transparent glass having a high release of calcium ions and fluorine ions. Because of its advantageous properties, the composite material can be used in particular as dental material.

There continues to be a great need in dentistry to prevent the secondary caries which frequently occurs after the use of dental restoration material, such as a filling composite. For this reason, filling composites which can release ions, such as fluorine, calcium or hydroxyl ions, in the oral cavity have also been investigated in recent years. These ions are advantageous since they have a remineralizing, bioactive or cariostatic action.

Restorative dental materials which develop a caries-inhibiting action because they contain sources of fluoride, such as special chlorohexidine-fluoride compounds, are known e.g. from U. Salz, Phillip Journal 14 (1997) 296.

Further examples of ion-releasing filling materials are glass ionomer cements or compomers whose organic matrix is always made of monomers, oligomers or polymers with carboxyl groups (cf. inter alia: A. D. Wilson, J. W. McLean, Glass Ionomer Cement, Quintessence Publishers, Chicago 1988; J. Nicholson, M. Anstice, Trends Polym. Sci. 2 (1994) 272; R. Hickel, L. Kremers, C. Haffner, Quintessenz 47 (1996) 1581).

Although these filling materials display a high degree of ion release, a clear reduction in the mechanical properties, in particular in strength, occurs in them after prolonged contact with water.

Furthermore, there is known from EP-B-449 399 a dental composite material which is used as relining material or as cement. In addition to customary (meth)acrylates the composite material contains a special glass which releases calcium ions and hydroxyl ions. However, the glass has too high an opacity, so that it gives the composite material an unnaturally dead appearance and therefore cannot be used in the field of aesthetically demanding restorations. The low translucence also prevents a light-curing of the composite material, so that a high through-curing depth, which is precisely what is needed in the case of filling materials for deep cavities, cannot be achieved. Finally, the glass also contains only very small quantities of fluorine which may come from cryolite, NaF or KF which is optionally used as flux.

The object of the invention is accordingly to make available a polymerizable composite material which, in addition to a high release of calcium ions, also displays a high release of fluorine ions upon contact with water, is fully cured by light even in deep layers and displays a high translucence which makes possible its use as a material for aesthetically demanding dental restorations.

This object is surprisingly achieved by the polymerizable composite material according to claims 1 to 9. The invention also relates to the transparent glass according to claim 10 and to the use of the composite material according to claims 11 and 12.

The polymerizable composite material according to the invention is characterized in that it contains
(a) at least one polymerizable monomer and
b) at least one transparent glass having a high release of calcium ions and fluorine ions, which contains the following components:

| Component | wt.-% |
|---|---|
| $SiO_2$ | 24.0 to 56.0 |
| CaO | 26.0 to 57.0 |
| F | 4.0 to 14.0. |

The glass used according to the invention preferably contains in addition at least one of the following components

| Component | wt.-% |
|---|---|
| $Na_2O$ | 1.0 to 9.0 |
| $B_2O_3$ | 1.0 to 14.0 |
| MgO | 1.0 to 14.0 |
| SrO | 1.0 to 12.0 |
| ZnO | 1.0 to 7.0 |
| $Al_2O_3$ | 0.5 to 5.0 |
| $ZrO_2$ | 0.5 to 4.0. |

Preferred quantity ranges exist for the individual components of the glass. These can be chosen independently of one another and are as follows

| Component | wt.-% |
|---|---|
| $SiO_2$ | 30.0 to 54.0, in particular 36.0 to 54.0 |
| CaO | 32.0 to 50.0 |
| F | 5.0 to 12.0 |
| $Na_2O$ | 1.0 to 8.0 |
| $B_2O_3$ | 1.0 to 12.0 |
| MgO | 1.0 to 10.0 |
| SrO | 1.0 to 10.0 |
| ZnO | 1.0 to 5.0 |
| $Al_2O_3$ | 0.5 to 4.0 |
| $ZrO_2$ | 0.5 to 4.0. |

Particularly preferred quantity ranges of the components of the glass, which can be chosen independently of one another, are as follows

| Component | wt.-% |
|---|---|
| $SiO_2$ | 45.0 to 54.0 |
| CaO | 35.0 to 50.0 |
| F | 6.0 to 12.0 |
| $Na_2O$ | 4.0 to 7.0 |
| $B_2O_3$ | 1.0 to 12.0 |
| MgO | 1.0 to 10.0 |
| SrO | 1.0 to 10.0 |
| ZnO | 1.0 to 5.0 |
| $Al_2O_3$ | 0.5 to 4.0 |
| $ZrO_2$ | 0.5 to 4.0. |

All the quantities that are given above and in the following in the description and in the claims of the components of the glass are to be understood as values which were obtained as follows: the quantities of the oxides were ascertained by quantitative analysis of the corresponding cations, i.e. Si, Ca, Na, B, Mg, Sr, Zn, Al and Zr, by means of X-ray fluorescence analysis and conversion of the obtained values into the quantities of the respective oxides. Thus the level of a cation serves to deduce the level of the corresponding oxide. In contrast to this, the quantity of F is determined directly by means of an electrode which is selective for fluoride ions after the glass had been subjected to a fusion with soda-potash dissolution.

As a result of the high F-contents of the glasses, they contain fluorides, such as $CaF_2$, to a notable extent. Therefore, the oxide contents calculated from the cation contents and accordingly the absolute oxygen content of the glass are too high, and the sum of the components exceeds 100%. The portion going beyond 100% is therefore usually referred to as so-called "fluorine-equivalent oxygen". This is customary for silicate glasses containing fluoride and is described at length e.g. in J. Lange "Rohstoffe der Glasindustrie", Deutscher Verlag für Grundstoff-industrie, Leipzig, Stuttgart (1993), pp. 221–223.

It is generally customary in glass manufacture to add small quantities of fluorides as flux in order to improve the melting behaviour of the glass in question. This is also, as described at the outset, known in the case of glasses for conventional dental materials. However, the overall structure of the glasses is not substantially changed by these small portions of fluorine.

In contrast to this, a high fluorine portion of at least 4,0 wt.-% is built in in the transparent glass used according to the invention, which substantially changes the basic structure of the glass compared with corresponding glasses which are free from fluorine or have only small fluorine contents as a result of the use of flux. A marked degradation of the $SiO_4$ tetrahedron network structure of the glass occurs because of this high fluorine content and the simultaneous incorporation of other network modifying ions, such as $Ca^{2+}$ or $Na^+$. A glass structure forms which can no longer be explained by the classical network theory. The glass structure comes close to a new glass structure which is called "inverted glass structure". An inverted glass is understood to be a glass which has less than 50 mol.-% network-former material.

As a result of the changed structure, it is above all the refractive index of the glass which changes, and surprisingly a release of fluorine ions with a simultaneous release of calcium ions from the glass is also possible. When the composite material is used in the dental field, the desired alkaline action can thus be brought about in the oral cavity by the calcium ions together with carbonate in the saliva, and, through he fluorine ions, their known remineralizing action. Calcium ions also promote the remineralization process.

Furthermore, the high fluoride content of the glass brings about a marked reduction in its refractive index to values below 1.60 and preferably below 1.56. The organic matrix of the composite forming through curing of the polymerizable monomer has a very similar refractive index, for which reason the whole composite material can likewise be translucent or even transparent. This is of particular advantage if the composite material is to be used for the production of visible dental restorations, which naturally are to have similar optical properties to translucent natural dental material.

To produce the transparent glass used according to the invention, suitable raw materials, in particular oxides, carbonates and fluorides, are mixed and melted at temperatures of in particular 1000 to 1600° C. to form a glass. The glass melt that forms is then quenched by being poured into water. The obtained transpa- rent glass frit is ground and dried and can then be combined with polymerizable monomer to give the polymerizable composite material according to the invention.

The glass is customarily used as powder, the average size of the particles being 1 to 100 μm as a rule and preferably 10 to 30 μm, relative to the number of particles.

In addition to the glass, the composite material can also contain customary filler components, such as amorphous spherical materials on the basis of mixed oxides from $SiO_2$, $ZrO_2$ and/or $TiO_2$, microfine fillers, such as pyrogenic silica or precipitation silica, as well as macro- or mini-fillers, such as quartz, glass ceramic or glass powder having an average particle size of 0.01 to 5 μm, and finally X-ray-opaque fillers such as ytterbium trifluoride.

The use of other glasses which release ions and are known e.g. for the production of glass ionomer cements is also possible. These are glass powders of customary fluoroaluminium silicate glasses with an average particle size of ca., 0.05 to 15 μm, which contain as principal constituents silicon oxide, aluminium oxide and calcium oxide (cf. A. D. Wilson, J. W. McLean, Glasionomerzement, Quintessenz Verlags-GmbH, 1988, Berlin, pages 21 et seq.).

The transparent glass and also the optionally present other inorganic constituents of the composite material can be silanized in customary manner in order to improve the bond between them and the organic matrix. Suitable as adhesion promoter is e.g. 3-methacryloyloxypropyl trimethoxy silane.

Apart from the special transparent glass described above which has a high release of calcium ions and fluorine ions, the polymerizable composite material according to the invention also contains at least one polymerizable monomer. Suitable monomers are the monomers themselves, polymerizable prepoly-mers produced therefrom as well as mixtures of these. Partic-ularly suitable as monomers are monofunctional or polyfunctional (meth)acrylates, which can be used alone or in mixtures. Coming into consideration as examples of these compounds are methyl methacrylate, isobutyl methacrylate, cyclohexyl meth-acrylate, triethylene glycol dimethacrylate, diethylene glycol dimethacrylate, tetraethylene glycol dimethacrylate, ethylene glycol dimethacrylate, polyethylene glycol dimethacrylate, butanediol dimethacrylate, hexanediol dimethacrylate, decane-diol dimethacrylate, dodecanediol dimethacrylate, bisphenol-A-dimethacrylate, trimethylolpropane trimethacrylate, ethoxylated bisphenol-A-dimethacrylate, but also bis-GMA (2,2-bis-4-(3-methacryloxy-2-hydroxypropyl)-phenylpropane) as well as the reaction products from isocyanates, in particular di- and/or triisocyanates, and OH-group-containing methacrylates, and the corresponding acrylates of all the above compounds. Examples of reaction products of isocyanates are the conversion prod-ucts of 1 mole of hexamethylene diisocyanate with 2 moles of 2-hydroxyethyl methacrylate, of 1 mole of (tri(6-isocyanato-hexyl)biuret with 3 moles of hydroxyethyl methacrylate and of 1 mole of trimethyl hexamethylene diisocyanate with 2 moles of hydroxyethyl methacrylate, which are also called urethane dimethacrylates.

A mixture of
(a) at least one non-acidic, non-ionic, hydrophilic crosslin-king monomer and
(b) at least one non-acid, non-ionic, hydrophilic dilution monomer having a viscosity of less than 1 Pas
is particularly preferably used as polymerizable monomer.

The term crosslinking monomers stands for monomers which contain at least two, preferably 2 to 4 groups capable of polymerization per monomer molecule.

The crosslinking monomers and the dilution monomers are hydrophilic, i.e. they are capable of hydrophilic interactions with the glass. Monomers which contain one or more, preferably 1 to 2 urethane and/or OH-groups, preferably OH-groups, are preferred. It was also found that these groups promote the transport of ions or the release of ions from the glass.

The term non-acidic compounds refers to monomers which cry no strongly acidic groups such as carboxyl, phosphoric acid, phosphonic acid, phosphinic acid or sulphonic acid groups and which preferably also contain no weakly acidic groups such as phenolic OH groups, SH groups or CH-acidic groups such as β-diketone groups or β-diketoester groups.

Non-ionic monomers within the meaning of this invention are those which contain no ionic groups such as cationic ammonium groups or sulphonium groups or anionic acid residue groups of the strongly acid groups named above.

Preferred crosslinking monomers are 2,2-bis-4-(3-methacryloxy-2-hydroxypropyl)-phenylpropane) (bis-GMA), i.e. the reaction product of glycidyl methacrylate and bisphenol-A (containing OH groups), and 7,7,9-trimethyl-4,13-dioxo-3,14-dioxa-5,12-diaza-hexadecan-1,16-diyl-dimethacrylate (UDMA), i.e. the urethane dimethacrylate made from 2 moles of 2-hydroxyethyl methacrylate (HEMA) and 1 mole of 2,2,4-trimethyl hexa-methylene diisocyanate (containing urethane groups). Also preferred as crosslinking monomers are reaction products of glycidyl methacrylate with other bisphenols, such as bisphenol-B (2,2'-bis-(4-hydroxyphenyl)-butane), bisphenol-F (2,2'-methylene diphenol) or 4,4'-dihydroxydiphenyl, as well as reaction products of 2 moles of HEMA or 2-hydroxypropyl-(meth)acrylate with, in particular 1 mole, of known diisocyanates, such as hexamethylene diisocyanate, m-xylylene diisocyanate or toluylene diisocyanate.

The term dilution monomers is taken to mean monomers having a viscosity of <1 Pas, preferably <100 mPas, which are suitable for diluting the generally highly viscous crosslinking monomers and thus permit the production of composites with a high filler content. The viscosity data relate to a temperature of 23° C. The viscosity is measured by means of a plate or rotation viscometer in accordance with DIN 53018.

The dilution monomers likewise contain at least two, preferably two to three groups capable of polymerization and at least one, preferably 1 to 2 OH groups and/or urethane groups, preferably OH groups.

A particularly preferred dilution monomer is glycerol dimethacrylate (GDMA). Other preferred dilution monomers can be produced by reaction of low-viscosity di- or triepoxides, such as for example ethylene glycol diglycidyl ether, glycerol triglycidyl ether or trimethylolpropane triglycidyl ether with (meth)acrylic acid. Further preferred are also the reaction products of 2 or 3 moles of methacrylic acid with glycerol triglycidyl ether or trimethylolpropane triglycidyl ether. The term "low-viscosity" stands for substances having a viscosity of <200 mPas, preferably <100 mPas (23° C.).

Preferred groups capable of polymerization are, for both the crosslinking monomers and dilution monomers, methacryl groups and/or acryl groups, in particular methacryl groups.

It was surprisingly found that, when using a mixture of crosslinking monomer (i) and dilution monomer (ii), composites are obtained which not only display a high degree of ion release but also suffer no substantial deterioration in their mechanical properties even after prolonged contact with water, such as storage in water. Moreover, corresponding composite pastes are very storage-stable even under a moist atmosphere. The uncured composite material can contain up to 1.0 wt.-% water without impairment of its stability in storage or of the mechanical properties of the cured material. This quite substantially facilitates both production and processing by the dentist or dental technician.

It is further preferred that the composite material contains at least 5 wt.-%, particularly preferably at least 10 wt.-% hydroxyl-group-containing monomers, i.e. monomers having at least one hydroxyl group per monomer molecule. It has also proved advantageous if the material according to the invention has, as a maximum, 2 wt.-% of monofunctional monomers, i.e. monomers having only one unsaturated group capable of polymerization, such as for example 2-hydroxyethyl(meth)acrylate.

The composite material according to the invention customarily also contains a polymerization catalyst (c). The composite material can be cured hot, cold or by photopolymerization, depending on the type of catalyst used. However, combinations of these are also possible (dual curing).

The known peroxides such as dibenzoyl peroxide, dilauroyl peroxide, tert.-butyl peroctoate or tert.-butyl perbenzoate can be used as catalysts for hot polymerization, but α,α-azo-bis-(isobutyroethyl ester), benzpinacol and 2,2'-dimethyl-benzpinacol are also suitable.

Usable as catalysts for the preferred photopolymerization are e.g. benzophenone and its derivatives, acylphosphinic oxides as well as benzoin and its derivatives. Examples of preferred photoinitiators are the α-diketones such as 9,10-phenanthrene-quinone, diacetyl, furil, anisil, 4,4'-dichlorobenzil and 4,4'-dialkoxybenzil. Camphor quinone is particularly preferably used.

The use of the photoinitiators together with a reducing agent is preferred. Examples of reducing agents are amines such as cyanoethylmethylaniline, dimethylamino-ethyl methacrylate, triethylamine, triethanolamine, N,N-dimethylaniline, N-methyldip-henylamine and N,N-dimethyl-sym.-xylidine, N,N-dimethyl-p-toluidine and p-dimethylamino benzoic acid ethyl ester. The photoinitiators and reducing agents can be used as catalyst mixtures together with catalysts for hot polymerization (preferred with peroxides).

Systems which deliver radicals, e.g. benzoyl or lauroyl peroxide together with amines such as N,N-dimethyl-sym.-xylidine, N,N-di-2-hydroxyethyl-p-toluidine or N,N-dimethyl-p-toluidine are used as catalysts for cold polymerization.

The quantities of polymerizable monomers (a), transparent glass (b) and polymerization catalyst together with optionally used activator (c) used in the composite material are in particular as follows:

(a) 15 to 70 wt.-%, preferably 20 to 45 wt.-% polymerizable monomers, (b) 20 to 85 wt.-%, preferably 40 to 60 wt.-% transparent glass, (c) 0.01 to 5.0 wt.-%, preferably 0.1 to 2.0 wt.-% polymerization catalyst and optionally present activator.

The details in wt.-% relate to the composite material.

The composite material according to the invention is preferably used as dental material. Its special properties play a special part for this, and it is precisely the high translucence, as well as the high release of calcium ions and fluorine ions upon contact with an aqueous medium, in particular in the oral cavity, which is to be emphasized. As a result of the high translucence, the composite material is particularly well suited for restoration materials which are intended to resemble the natural tooth material after curing. In addition, the high translucence permits the provision of exclusively light-curing materials having a very high through-curing depth, so that they can even be used as filling material for deep cavities. The high release of ions finally leads to an inhibition of secondary caries.

It must also be emphasized that the cured composite material according to the invention surprisingly suffers only an insignificant change in mechanical properties, such as strength and E-modulus, even in the case of prolonged contact with water.

When the composite material is used as dental material, it is applied to the area of a natural or artificial tooth that is to be treated, optionally shaped and then cured by polymerization. The composite material is quite particularly preferably used as a restorative material, such as filling material for cavities.

The invention is described further in the following by examples.

EXAMPLES

Examples 1 to 16

A total of 16 transparent glasses having a high release of calcium ions and fluorine ions were produced that were usable in the composite material according to the invention. To produce the glasses, suitable oxides, carbonates and fluorides were homogeneously mixed to produce a batch. This batch was melted in a platinum-rhodium crucible at a temperature of 1100 to 1450° C. during a homogenization time of 30 minutes to 3 hours to produce a glass melt. The glass melt was then quenched by being poured into water. The obtained transparent glass frit was dried and ground to the desired particle size.

The respective chemical composition of the individual glasses is given in the following Table I, the quantities of the individual components being determined by analysis of the glass in the way that was described above. The refractive index, the melting temperature as well as the appearance of the glass are also given.

In all cases, transparent glasses with a refractive index of <1.60 were obtained.

The examples show that glasses having different refractive indices can be produced by altering the chemical composition. The refractive index of the glass can thereby be matched to that of the organic matrix of the composite material. In this way, by combining the glasses with suitable polymerizable monomers or mixtures thereof, a composite material can be produced that cures to give a translucent material which satisfies the high optical requirements for aesthetically demanding restorative dental materials.

TABLE I (quantities in wt. %)

| Example | $SiO_2$ | CaO | MgO | SrO | ZnO | $Na_2O$ | $Al_2O_3$ | $B_2O_3$ | $ZrO_2$ | F | $\Sigma_1$ | F-equivalent oxygen | $\Sigma_2$ | $n_D$ | Melting temperature and appearance of the glass |
|---|---|---|---|---|---|---|---|---|---|---|---|---|---|---|---|
| 1 | 55.8 | 32.1 | | | | 6.6 | | | | 9.5 | 104 | −4.0 | 100 | 1.5580 | 1400° C.; transparent, opalescent |
| 2 | 30.2 | 47.3 | 4.7 | | | 3.8 | | 8.5 | | 9.5 | 104 | −4.0 | 100 | 1.5736 | 1200° C.; transparent |
| 3 | 48.7 | 38.2 | | | | 5.0 | | | 3.9 | 7.3 | 103.1 | −3.1 | 100 | 1.5604 | 1250° C.; transparent |
| 4 | 52.6 | 33.5 | 3.8 | | | 5.7 | | | | 7.6 | 103.2 | −3.2 | 100 | 1.5427 | 1250° C.; transparent |
| 5 | 48.6 | 42.9 | | | | 4.2 | | | | 7.6 | 103.3 | −3.3 | 100 | 1.5582 | 1250° C.; transparent |
| 6 | 41.5 | 38.7 | 10.9 | | | 4.6 | | | | 7.5 | 103.2 | −3.2 | 100 | 1.5750 | 1200° C.; transparent |
| 7 | 47.4 | 39.8 | | | | 8.4 | | | | 7.6 | 103.2 | −3.2 | 100 | 1.5450 | 1250° C.; transparent |
| 8 | 42.3 | 43.2 | | | | 6.5 | | | | 14.0 | 106.0 | −6.0 | 100 | 1.5533 | 1200° C.; transparent |
| 9 | 49.6 | 39.4 | | | | 4.7 | 1.9 | | | 7.6 | 103.2 | −3.2 | 100 | 1.5685 | 1450° C.; transparent |
| 10 | 50.2 | 26.0 | | 11.5 | | 8.3 | | | | 6.8 | 102.8 | −2.8 | 100 | 1.5380 | 1300° C.; transparent |
| 11 | 51.3 | 40.9 | | | | 4.9 | | | | 4.9 | 102.0 | −2.0 | 100 | 1.5707 | 1350° C.; transparent |
| 12 | 46.5 | 37.5 | | | 6.7 | 5.2 | | | | 7.2 | 103.1 | −3.1 | 100 | 1.5580 | 1280° C.; transparent |
| 13 | 51.8 | 40.1 | | | | 5.9 | | | | 4.0 | 101.8 | −1.8 | 100 | 1.5755 | 1400° C.; transparent |
| 14 | 24.0 | 42.6 | 14.0 | | | | 14.0 | | | 9.5 | 104.0 | −4.0 | 100 | 1.5830 | 1200° C.; transparent |
| 15 | 48.2 | 38.3 | | | | 5.0 | 4.2 | | | 7.5 | 103.2 | −3.2 | 100 | 1.5516 | 1250° C.; transparent |
| 16 | 24.0 | 56.6 | | | | | 14.0 | | | 9.5 | 104.0 | −4.0 | 100 | 1.5922 | 1250° C.; transparent |

$\Sigma_1$ = total quantity of all oxides including fluorine
$\Sigma_2$ = total quantity of all oxides including fluorine and less the fluorine-equivalent oxygen

Example 17

Monomer mixtures of the following composition were used for the production of composite materials according to the invention.

| Monomer | Mixture (in wt.-%) | |
| --- | --- | --- |
| | A | B |
| bis-GMA[1] | 39.0 | 42.0 |
| UDMA[2] | 30.0 | 37.1 |
| GDMA[3] | 30.0 | — |
| TEGDMA[4] | — | 20.1 |
| Catalyst | 1.0 | 0.8 |

[1]2,2-bis-4-(3-methacryloxy-2-hydroxyproypl)-phenylpropane
[2]Urethane methacrylate obtainable by reaction of 2 moles of 2-hydroxyethyl methacrylate and 1 mole of 2,2,4-trimethyl-hexamethylene diisocyanate
[3]Glycerol dimethacrylate
[4]Triethylene glycol dimethacrylate Using the two prepared monomer mixtures A and B, corresponding composite pastes A and B were prepared by thorough mixing with transparent glass used according to the invention plus other fillers. The composite pastes had the composition which can be seen from the following table.

| Component | Composite (in wt.-%) | |
| --- | --- | --- |
| | A | B |
| Monomer mixture | 22.0 | 22.1 |
| Transparent glass[1] | 48.0 | 52.2 |
| SP-2034, sil.[2] | 11.0 | — |
| YbF$_3$ | 12.0 | 10.0 |
| Aerosil-OX-50 sil.[3] | 4.0 | 3.8 |
| HDK-2000[4] | 3.0 | 2.4 |
| Ba-glass sil. (GM 27884)[5] | — | 9.5 |

[1]Glass according to Example 7 from Table I which was silanized in the usual way.
[2]Silanized fluotine-calcium-aluminium silicate glass.
[3]Silanized pyrogenic silica (Degussa, Hanau)
[4]Highly-dispersed precipitation silica (Wacker, Burghausen)
[5]Silanized barium-aluminium silicate glass (Schott, Landshut)

Testpieces were formed from the two composite pastes to determine the mechanical properties and the fluoride release, and cured twice for 3 minutes with the light of a customary dental polymerization lamp, namely an Spectramat from Ivoclar AG, Liechtenstein.

Composite A
Mechanical Properties

| a) | Bending strength: | 24 h H$_2$O storage: | 122 MPa |
| --- | --- | --- | --- |
| | | 6 d H$_2$O storage + 24 h boiling: | 117 MPa |
| b) | Bending E modulus: | 24 h H$_2$O storage: | 11.4 GPa |
| | | 6 d H$_2$O storage + 24 h boiling: | 11.3 GPa |

The bending strength and the bending E-modulus were determined in accordance with ISO standard 4049 (1988).
Release of F Ions (Cumulative)
After 28 days (lactate buffer, 37° C.): 218 $\mu g/cm^{-2}$.
To establish the fluoride-release capacity, cured testpieces (diameter=20 mm, Height=1.5 mm) were stored in 30 ml of lactate buffer solution at 37° C. in the agitator and the amount of released fluoride was measured after specific intervals using a fluorine electrode.
In comparison to this, composite B shows a fluoride release of 124 $\mu g/cm^{-2}$ under identical conditions. The reason for this somewhat reduced, but still high, emission of fluoride is that in the case of composite B, instead of the particularly preferred hydrophilic glycerol dimethacrylate, the hydrophobic triethylene glycol dimethacrylate was used as dilution monomer.

For further comparison, the release of fluorine ions from a compomer customary in the trade, namely Compoglass® from Ivoclar AG, Liechtenstein, and from a glass ionomer cement customary in the trade, namely Vivaglass Fil from Ivoclar AG, Liechtenstein, was determined. These were ca. 22 $\mu g/cm^{-2}$ for Compoglass and ca. 240 $\mu g/cm^{-2}$ for Vivaglass Fil.

This comparison proves that the composite material according to the invention is also superior to conventional compomers in terms of the release of fluorine ions and achieves similar values to the glass ionomer cements which are particularly efficient in this respect.

What is claimed is:
1. A polymerizable composite material, which comprises:
    (a) at least one polymerizable monomer, which comprises a mixture of at least one non-acidic, non-ionic, hydrophilic crosslinking monomer and at least one non-acidic, non-ionic, hydrophilic dilution monomer having a viscosity of less than 1 Pas and, which comprises at least 5 wt.-% of hydroxyl-group-containing monomers;
    (b) at least one transparent glass having a high release of calcium ions and fluorine ions, which contains the following components:

| Component | wt.-% |
| --- | --- |
| SiO$_2$ | 24.0 to 56.0 |
| CaO | 26.0 to 57.0 |
| F | 4.0 to 14.0, | wherein the glass additionally contains at least one of the following components:

| Component | wt.-% |
| --- | --- |
| Na$_2$O | 1.0 to 9.0 |
| B$_2$O$_3$ | 1.0 to 14.0 |
| MgO | 1.0 to 14.0 |
| SrO | 1.0 to 12.0 |
| ZnO | 1.0 to 7.0 |
| Al$_2$O$_3$ | 0.5 to 5.0 |
| ZrO$_3$ | 0.5 to 4.0, and | wherein the glass has a refractive index of less than 1.60; and
    (c) a polymerization catalyst.
2. A composite material according to claim 1, wherein the refractive index is less than 1.56.
3. A composite material according to claim 1, wherein the components of the glass are present independently of one another in the following quantities

| Component | wt.-% |
| --- | --- |
| SiO$_2$ | 30.0 to 54.0, |
| CaO | 32.0 to 50.0 |
| F | 5.0 to 12.0. | and wherein the components of the glass further comprise the following components which are present independently of the other components in the following quantities

| | |
|---|---|
| Na$_2$O | 1.0 to 8.0 |
| B$_2$O$_3$ | 1.0 to 12.0 |
| MgO | 1.0 to 10.0 |
| SrO | 1.0 to 10.0 |
| ZnO | 1.0 to 5.0 |
| Al$_2$O$_3$ | 0.5 to 4.0 |
| ZrO$_2$ | 0.5 to 4.0. |

4. A composite material according to claim 3, wherein the components of the glass are present independently of one another in the following quantities

| Component | wt.-% |
|---|---|
| SiO$_2$ | 45.0 to 54.0 |
| CaO | 35.0 to 50.0 |
| F | 6.0 to 12.0 |
| Na$_2$O | 4.0 to 7.0 |
| B$_2$O$_3$ | 1.0 to 12.0 |
| MgO | 1.0 to 10.0 |
| SrO | 1.0 to 10.0 |
| ZnO | 1.0 to 5.0 |
| Al$_2$O$_3$ | 0.5 to 4.0 |
| ZrO$_2$ | 0.5 to 4.0. |

5. A composite material according to claim 3, wherein SiO$_2$ is present in an amount from 36.0 to 54.0 wt %.

6. A composite material according to claim 1, wherein said crosslinking monomer comprises 2,2-bis-4-(3-methacryl-oxy-2-hydroxypropyl)-phenylpropane) (bis-GMA); 7,7,9-trimethyl-4,13-dioxo-3,14-dioxa-5,12-diazahexa-decan-1,16-diyl-dimethacrylate (UDMA); a reaction product of glycidyl methacrylate with a bisphenol; or a reaction product of 2 moles of 2-hydroxyethyl methacrylate (HEMA) or 2-hydroxypropyl-(meth)acrylate with 1 mole of diisocyanate.

7. A composite material according to claim 1, wherein said dilution monomer comprises glycerol dimethacrylate (GDMA), a reaction product of low-viscosity di- and triepoxides with (meth)acrylic acid, or a reaction product of 2 or 3 moles of methacrylic acid with glycerol triglycidyl ether or tri-methylolpropane triglycidyl ether.

* * * * *